US011670017B2

United States Patent
Riddell et al.

(10) Patent No.: US 11,670,017 B2
(45) Date of Patent: Jun. 6, 2023

(54) SYSTEMS AND METHODS FOR REPROJECTION AND BACKPROJECTION VIA HOMOGRAPHIC RESAMPLING TRANSFORM

(71) Applicant: GE Precision Healthcare LLC, Milwaukee, WI (US)

(72) Inventors: Cyril Riddell, Issy-les-Moulineaux (FR); Marion Savanier, Versailles (FR); Emilie Chouzenoux, Paris (FR); Jean-Christophe Pesquet, Romainvilliers (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 370 days.

(21) Appl. No.: 16/945,539

(22) Filed: Jul. 31, 2020

(65) Prior Publication Data
US 2022/0036605 A1 Feb. 3, 2022

(51) Int. Cl.
*G01T 1/00* (2006.01)
*A61B 6/00* (2006.01)
*G06T 11/00* (2006.01)
*A61B 6/03* (2006.01)

(52) U.S. Cl.
CPC ............ *G06T 11/005* (2013.01); *A61B 6/032* (2013.01); *A61B 6/4208* (2013.01); *A61B 6/5217* (2013.01); *G06T 11/006* (2013.01); *G06T 2210/41* (2013.01); *G06T 2211/424* (2013.01)

(58) Field of Classification Search
CPC . G06T 11/005; G06T 11/006; G06T 2210/41; G06T 2211/416; G06T 2211/424; A61B 6/5205
See application file for complete search history.

(56) References Cited

U.S. PATENT DOCUMENTS

2004/0013294 A1\* 1/2004 Bernard De Man . G06T 11/008
378/4

OTHER PUBLICATIONS

Long, Y. et al., "3D Forward and Back-Projection for X-Ray CT Using Separable Footprints," IEEE Transactions on Medical Imaging, vol. 29, No. 11, Nov. 2010, 27 pages.
Wu, M. et al., "GPU Acceleration of 3D Forward and Backward Projection Using Separable Footprints for X-ray CT Image Reconstruction," Proceedings of the 11th International Meeting on Fully Three-Dimensional Image Reconstruction in Radiology and Nuclear Medicine, Jul. 11, 2011, Potsdam, Germany, 4 pages.

(Continued)

*Primary Examiner* — Dani Fox
(74) *Attorney, Agent, or Firm* — McCoy Russell LLP

(57) ABSTRACT

Systems and methods are provided for reprojection and back projection of objects of interest via homographic transforms, and particularly one-dimensional homographic transforms. In one example, a method may include acquiring imaging data corresponding to a plurality of divergent X-rays, assigning a single functional form to the plurality of divergent X-rays, determining, via a homographic transform, weights of interaction between a plurality of distribution samples and a plurality of X-ray detector bins based on the single functional form, and reconstructing an image based on the weights of interaction.

18 Claims, 4 Drawing Sheets

(56) References Cited

OTHER PUBLICATIONS

Schlifske, D., "Fast GPU-Based Approach to Branchless Distance-Driven Projection and Back-Projection in Cone Beam CT," Master of Science Thesis, Marquette University, Dec. 2015, 81 pages.

Mitra, A. et al., "Fast Parallel GPU Implementation for Clinical Helical CT using Branchless DD," Proceedings of the GPU Technology Conference, Apr. 4, 2016, San Jose, California, 2 pages.

Xie, X et al., "Accelerating Separable Footprint (SF) Forward and Back Projection on GPU," Proceedings of SPIE Medical Imaging 2017: Physics of Medical Imaging, vol. 10132, Jun. 5, 2017, 8 pages.

Liu, R. et al., "GPU-based Branchless Distance-Driven Projection and Backprojection," IEEE Transactions on Computational Imaging, vol. 4, No. 4, Dec. 2017, 48 pages.

Chapdelaine, C. et al., "New GPU implementation of Separable Footprint (SF) Projector and Backprojector: first results," HAL Archives Website, Available Online at https://hal.archives-ouvertes.fr/hal-01745746/document, May 2018, 5 pages.

EP application 21187533.1 filed Jul. 23, 2021—extended Search Report dated Mar. 31, 2022; 8 pages.

Riddell C et al: "Rectification for Cone-Beam Projection and Backprojection", IEEE Transactions on Medical Imaging, IEEE, USA, vol. 25, No. 7, Jul. 2006 (Jul. 2006), pp. 950-962, XP001545927, ISSN: 0278-0062, DOI: 10.1109/TMI.2006.876169 * the whole document *.

Savanier Marion et al: "A Matched CBCT Projector-Backprojector Based on the Convolution of B-splines", The 6th International Conference on Image Formation in X-Ray Computed Tomography, Aug. 3, 2020 (Aug. 3, 2020), XP055902877, Regensburg * the whole document *.

* cited by examiner

SYSTEMS AND METHODS FOR REPROJECTION AND BACKPROJECTION VIA HOMOGRAPHIC RESAMPLING TRANSFORM

FIELD

Embodiments of the subject matter disclosed herein relate to medical imaging, and more particularly to reprojection and backprojection of objects of interest via one-dimensional homographic resampling transforms.

BACKGROUND

Computed tomography (CT) may be used as a non-invasive medical imaging technique. Specifically, CT imaging data acquisition may include passing X-ray beams through an object, such as a patient, such that the X-ray beams are attenuated and then collecting the attenuated X-ray beams at an X-ray detector array. The acquired CT imaging data may be a set of line integral measurements corresponding to a distribution of attenuation coefficients of the object. The distribution may be reconstructed from the set of line integral measurements as a viewable image via a backprojection, or backward projection, step in an analytical or an iterative reconstruction algorithm. In the case of the iterative reconstruction algorithm, the reconstructed distribution may then be mapped onto an updated set of computed line integrals via a reprojection, or forward projection, step, whereafter backprojection and reprojection steps may be iterated as desired.

A tomographic operator or projector may be selected to encode a geometric representation of lines of integration corresponding to the CT imaging data. For the backprojection step, this may be algebraically represented as:

$$f_j = \sum_{i=1}^{I} r_{ij} p_i \quad (1)$$

where $p_i$ is an ith line integral measurement of I line integral measurements and $r_{ij}$ is an element of a matrix formulation R of the tomographic operator which backprojects the ith measurement to a sampling point $f_j$ corresponding to a jth attenuation coefficient (that is, the attenuation coefficient at the jth sampling point of J sampling points). The adjoint (transpose, since R is real) operation constitutes the reprojection step, represented as:

$$p_i = \sum_{j=1}^{J} r_{ij} f_j \quad (2)$$

Numerous such geometry-based models exist for image reconstruction, selection of which dictates precision and therefore final image quality. Computational speed is an additional factor, which may be accomplished by massive parallelization, e.g., on graphics processing units (GPUs). However, geometry-based models may be difficult to implement and scale across GPU computing frameworks. Both precision and computational speed may be key factors in driving image reconstruction via deep learning techniques.

BRIEF DESCRIPTION

In one embodiment, a method may include acquiring imaging data corresponding to a plurality of divergent X-rays, assigning a single functional form to the plurality of divergent X-rays, determining, via a homographic transform, weights of interaction between a plurality of distribution samples and a plurality of X-ray detector bins based on the single functional form, and reconstructing an image based on the weights of interaction.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
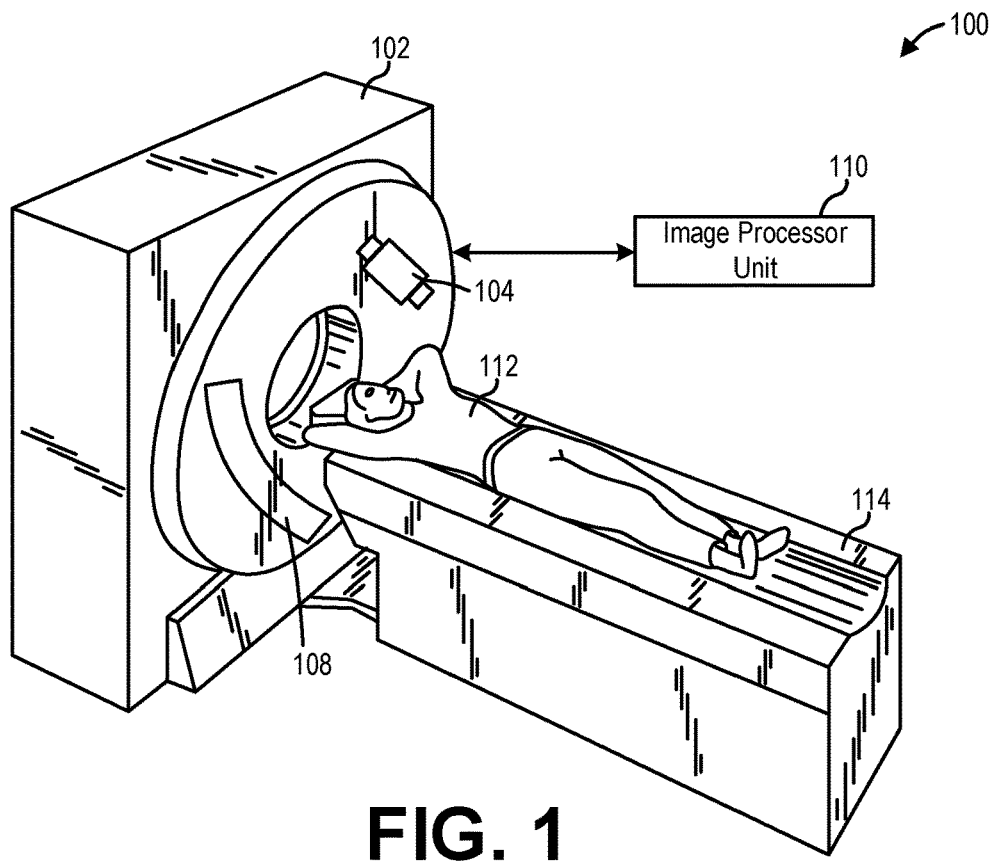
FIG. 1 shows a pictorial view of an exemplary medical imaging system, according to an embodiment.
Figure 2:
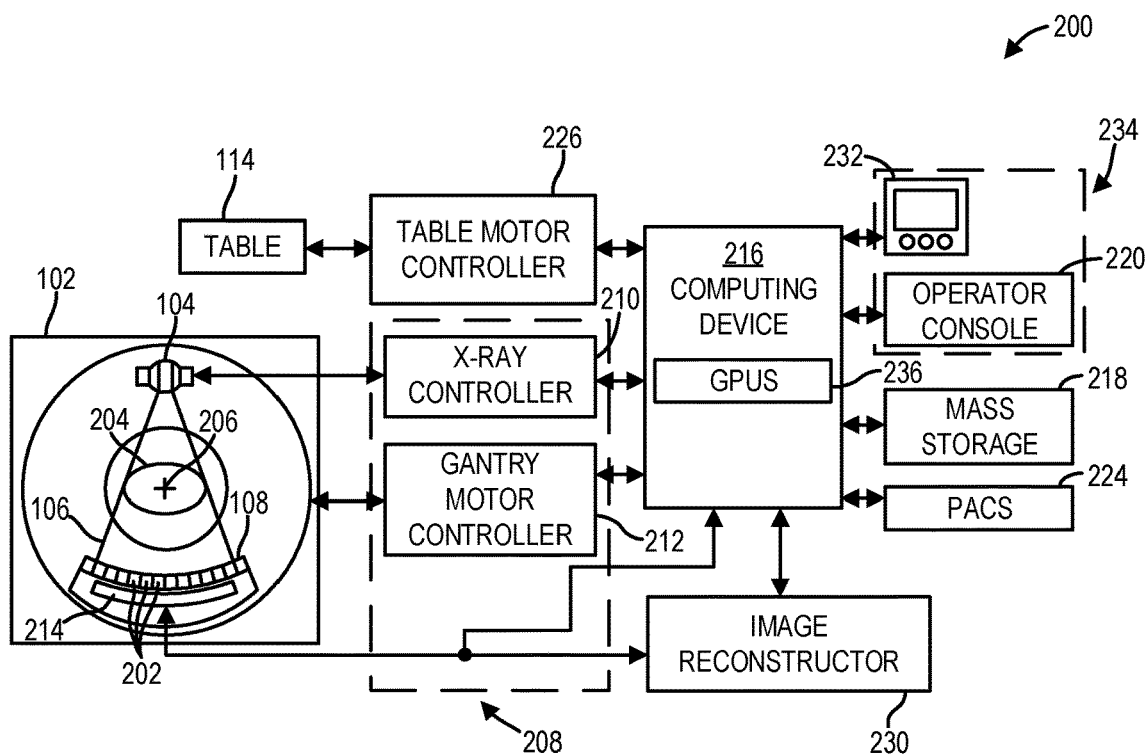
FIG. 2 shows a schematic block diagram of the exemplary medical imaging system, according to an embodiment.

The following description relates to various embodiments of medical imaging systems, and of methods for reprojecting and backprojecting objects of interest via symmetric projector/backprojector operator pairs. One such medical imaging system configured to acquire computed tomography (CT) medical imaging data is depicted in FIGS. 1 and 2, and one such method for (iterative) reprojection and backprojection via a symmetric projector/backprojector operator pair is provided in FIG. 6, from which a reconstructed image may be precisely and efficiently obtained on a massively parallel computing architecture, e.g., a plurality of graphics processing units (GPUs).

Images of an object of interest may be reconstructed from a plurality of line integral measurements via an analytical or an iterative reconstruction method. Each method leverages a backprojection operator or backprojector to map the plurality of line integral measurements to a distribution of attenuation coefficients of the object of interest. Iterative reconstruction methods may further leverage the adjoint of the backprojector, referred to as a projection operator or projector, to recast the distribution of attenuation coefficients as a plurality of computed line integrals than may be compared to the line integral measurements.

Figure 3:
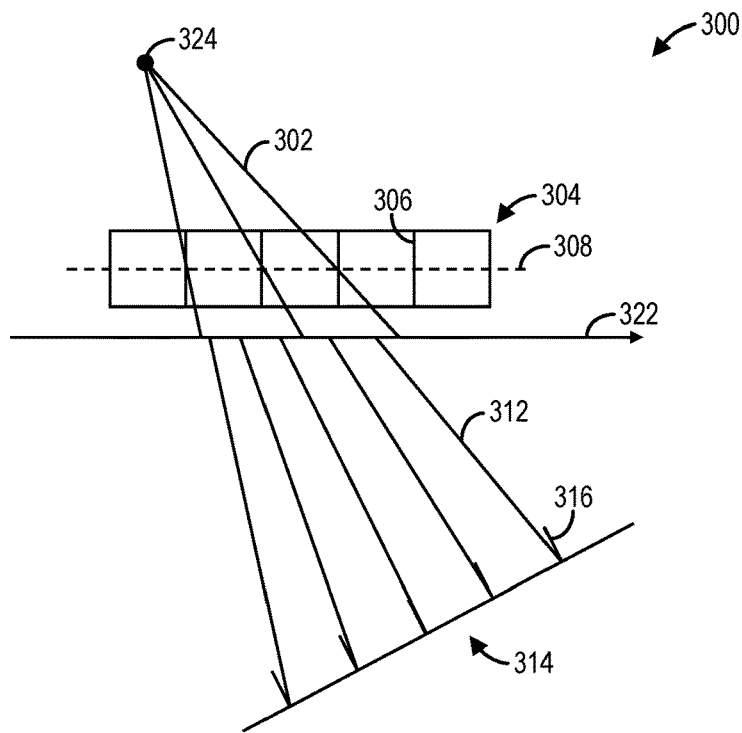
FIG. 3 shows a schematic diagram of an exemplary geometry-based distance-driven image reconstruction model.

The projector/backprojector pair may encode a geometric representation of a plurality of lines of integration along which the plurality of line integral measurements is taken. Geometry-based image reconstruction models may leverage the geometric representation to reconstruct a distribution of attenuation coefficients of a given object of interest, from which a viewable image may be obtained. One example of such a geometry-based image reconstruction model, the so-called distance-driven model, is schematically depicted in FIG. 3.

Depending on image reconstruction scheme (e.g., analytical or iterative), mathematical constraints as to symmetry of the projector/backprojector pair may limit selection of a suitable model. Though geometry-based image reconstruction models satisfy such constraints, computational scalability may be hampered as a result of inherent difficulties of implementation on massively parallel computing architectures.

Accordingly, in embodiments described herein, systems and methods are provided for resampling of continuous functions via homographic transforms. Aspects of one such homography-based image reconstruction model are discussed in the context of the exemplary flat-panel detector-based cone-beam tomographic geometry of FIG. 4A, and an exemplary one-dimensional homographic resampling transform is schematically depicted in FIG. 4B. As further schematically depicted in FIG. 5, leveraging homographic transforms in this way provides arbitrary levels of precision via basis set expansions of the continuous functions without sacrificing the symmetry of the projector/backprojector pair. As such, no assumptions have been made as to the geometric representation of the lines of integration. By recasting, or altogether avoiding, the geometric representation, issues with massively parallel implementation specific to the geometry-based image reconstruction models may be averted. Indeed, homography-based image reconstruction models may be advantageously suitable to parallelization where the geometry-based image reconstruction models are not. As a result, homography-based image reconstruction models may be easily adapted to deep learning paradigms for image reconstruction. In this way, a more generalized image reconstruction model is provided for symmetric reprojection and backprojection of objects of interest via homographic transforms.

One exemplary embodiment of an imaging system may include a massively parallel GPU architecture configured to determine coefficients of matrix representations of the projector/backprojector operator pair substantially in parallel. As such, the homography-based image reconstruction models described herein may enable more efficient processing of imaging data than geometry-based image reconstruction models (which may utilize loops which are difficult to parallelize, parallelizable to a more limited extent, or not parallelizable at all).

Further, the arbitrary levels of precision to which reprojection and backprojection may be executed by varying a size and structure of the basis set expansion may enable increased precision of the homography-based image reconstruction models relative to the geometry-based image reconstruction models, even while maintaining increases in processing efficiency via facile and massively parallelizable coefficient determination (as discussed above). In this way, the homography-based image reconstruction models described herein may provide a technical improvement to computer functionality by simultaneously improving processing efficiency and precision of image reconstruction algorithms. Moreover, implementations on the massively parallel GPU architecture may be well-suited for interfacing with deep learning image reconstruction techniques, which may further improve image fidelity. As such, in some embodiments, higher-fidelity reconstructed images may be generated, which may concomitantly promote greater accuracy in diagnosis of medical issues depicted by the reconstructed images.

Referring now to FIG. 1, an exemplary imaging system 100 is depicted according to an embodiment. In the illustrated embodiment, the imaging system 100 is an X-ray imaging system configured to perform CT imaging. Though the illustrated embodiment actively acquires medical images, it is understood that other embodiments do not actively acquire medical images. Instead, embodiments may retrieve images or imaging data that was previously acquired by an imaging system and process the imaging data as set forth herein.

The imaging system 100 may be configured to image a subject 112 such as a patient, an inanimate object, one or more manufactured parts, and/or foreign objects such as dental implants, stents, and/or contrast agents present within the body. In one embodiment, the imaging system 100 may include a gantry 102, which in turn, may further include at least one X-ray source 104 configured to project a beam of X-ray radiation 106 (see FIG. 2) for use in imaging the subject 112 laying on a table 114. Specifically, the X-ray source 104 may be configured to project the X-rays 106 towards a detector array 108 positioned on the opposite side of the gantry 102. Although FIG. 1 depicts a curved detector array 108, in certain embodiments, a flat-panel detector may be employed. Further, although FIG. 1 depicts a single X-ray source 104, in certain embodiments, multiple X-ray sources and/or detectors may be employed to project a plurality of X-ray radiation beams 106 for acquiring projection data corresponding to the subject 112 at different energy levels or angular orientations. In some CT imaging embodiments, the X-ray source 104 may enable dual-energy imaging by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set acquired at a low-kVp setting and the other acquired at a high-kVp setting. It should thus be appreciated that the methods described herein may be implemented with single energy acquisition techniques as well as dual energy acquisition techniques.

In certain embodiments, the imaging system 100 further includes an image processor unit 110 configured to reconstruct images of a target volume of the subject 112 using an iterative or analytic image reconstruction method, or a combination of both. For example, in some CT imaging applications, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR) or model-based iterative reconstruction (MBIR), and the like, to reconstruct images of a target volume of the subject 112. In some examples, the image processor unit 110 may use both an analytic image reconstruction approach such as FBP in addition to an iterative image reconstruction approach. In one embodiment, and as discussed in detail below, the image processor unit 110 may use an iterative image reconstruction approach leveraging one-dimensional homographic resampling transforms.

In some CT imaging system configurations, an X-ray source projects a cone-shaped X-ray radiation beam which is collimated to lie within an X-Y-Z plane of a Cartesian coordinate system (generally referred to as an "imaging plane"). The X-ray radiation beam passes through an object being imaged, such as the patient or subject. The X-ray radiation beam, after being attenuated by the object, impinges upon an array of radiation detectors. The intensity of the attenuated X-ray radiation beam received at the detector array is dependent upon the attenuation of an X-ray radiation beam by the object. Each detector element of the array produces a separate electrical signal that is a measurement (e.g., a line integral measurement) of the X-ray beam attenuation at the detector location. The attenuation measurements from all the detector elements are acquired separately to produce a transmission profile.

In some CT imaging systems, the X-ray source and the detector array are rotated with a gantry about the imaging plane and around the object to be imaged such that an angle at which the radiation beam intersects the object constantly changes. A group of X-ray radiation attenuation measurements, e.g., projection data, from the detector array at one angular position of the gantry is referred to as a "view." A "scan" of the object includes a set of views made at different angular positions, or view angles, during one revolution of the X-ray source and detector about the object. It is contemplated that the benefits of the methods described herein accrue to many medical imaging modalities, so as used herein the term "view" is not limited to the use as described above with respect to projection data from one gantry angle. The term "view" is used to mean one data acquisition whenever there are multiple data acquisitions from different angles, whether from a CT, X-ray radiographic imaging, positron emission tomography (PET), or single-photon emission CT (SPECT) acquisition, and/or any other modality including modalities yet to be developed as well as combinations thereof in fused embodiments.

The projection data is processed to reconstruct an image that corresponds to one or more two-dimensional slices taken through the object or, in some examples where the projection data includes extended axial coverage, e.g., Z-axis illumination, a three-dimensional image volume of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into integers (called "CT numbers" or "Hounsfield units" in the case of a CT imaging system), which are used to control the brightness of a corresponding pixel on a display device.

To reduce the total scan time, a "helical" scan may be performed. To perform a "helical" scan, the patient is moved while the data for the prescribed axial coverage is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein, the term "image" broadly refers to both viewable images and data representing a viewable image. However, many embodiments generate (or are configured to generate) at least one viewable image.

Referring now to FIG. 2, an exemplary imaging system 200 similar to the imaging system 100 of FIG. 1 is depicted. As shown, the imaging system 200 may include multiple components. The components may be coupled to one another to form a single structure, may be separate but located within a common room, or may be remotely located with respect to one another. For example, one or more of the modules described herein may operate in a data server that has a distinct and remote location with respect to other components of the imaging system 200.

In accordance with aspects of the present disclosure, the imaging system 200 may be configured for imaging a subject 204 (e.g., the subject 112 of FIG. 1). In one embodiment, the imaging system 200 may include the detector array 108 (see FIG. 1). The detector array 108 may further include a plurality of detector elements 202 that together sense the X-ray radiation beams 106 that pass through the subject 204 (such as a patient) to acquire corresponding projection data. Accordingly, in one embodiment, the detector array 108 may be fabricated in a multi-slice configuration including the plurality of rows of cells or detector elements 202. In such a configuration, one or more additional rows of the detector elements 202 may be arranged in a parallel configuration for acquiring the projection data.

The gantry 102 may movably support the X-ray source 104 and the detector array 108 mounted opposite to each other on opposed ends. The subject 204 may accordingly be disposed between the X-ray source 104 and the detector array 108, supported by the table 114.

It will be recognized that in some embodiments, the table 114 may further be movable to achieve a desired image acquisition. During such an acquisition of image data, the gantry 102 may be movable to change a position and/or orientation of the X-ray source 104 and/or the detector array 108 relative to the subject 204.

Accordingly, in some embodiments, the gantry 102 may remain fixed during a given imaging session so as to image a single 2D projection of the subject 204. In such embodiments, a position of the gantry 102 and/or the table 114 may be adjusted between imaging sessions so as to image another view of the subject 204.

In other embodiments, such as in CT imaging applications, the imaging system 200 may be configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In such embodiments, as the X-ray source 104 and the detector array 108 rotate, the detector array 108 may collect data of the attenuated X-ray beams. The data collected by the detector array 108 may undergo preprocessing and calibration to condition and process the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections may be converted to a set of material-density projections. The material-density projections may be reconstructed to form a pair or a set of material-density maps or images of each respective basis material, such as bone, soft tissue, and/or contrast agent maps. The material-density maps or images may be, in turn, associated to form a volume rendering of the basis material, for example, bone, soft tissue, and/or contrast agent, in the imaged volume.

Once reconstructed, the basis material image produced by the imaging system 200 may reveal internal features of the subject 204, expressed in the densities of two basis materials. The density image, or combinations of multiple density images, may be displayed to show these features. In traditional approaches to diagnosis of medical conditions, such as disease states, and more generally of medical events, a radiologist or physician would consider a hard copy or display of the density image, or combinations thereof, to discern characteristic features of interest. Such features might include lesions, sizes and shapes of particular anatomies or organs, and other features that would be discernable in the image based upon the skill and knowledge of the individual practitioner.

In one embodiment, the imaging system 200 may include a control mechanism 208 to control movement of the components such as rotation of the gantry 102 and the operation of the X-ray source 104. In certain embodiments, the control mechanism 208 may further include an X-ray controller 210 configured to provide power and timing signals to the X-ray source 104. Additionally, the control mechanism 208 may include a gantry motor controller 212 configured to control a rotational speed and/or position of the gantry 102 or of various components thereof (e.g., the X-ray source 104, the detector array 108, etc.) based on imaging requirements.

In certain embodiments, the control mechanism 208 may further include a data acquisition system (DAS) 214 configured to sample analog data received from the detector elements 202 and convert the analog data to digital signals for subsequent processing. For photon-counting imaging systems, the DAS 214 may download measured photon counts in one or more energy bins from detector array 108. The DAS 214 may further be configured to selectively aggregate analog data from a subset of the detector elements 202 into so-called macro-detectors, as described further herein.

The data sampled and digitized by the DAS 214 may be transmitted to a computer or computing device 216. In the illustrated embodiment, the computing device 216 may be configured to interface with various components of the imaging system 200. As such, the computing device 216 may be configured to control operation of the imaging system 200. In various embodiments, the computing device 216 may take the form of a mainframe computer, server computer, desktop computer, laptop computer, tablet device, network computing device, mobile computing device, mobile communication device, etc. In one embodiment, the computing device 216 may take the form of an edge device for interfacing between the various components of FIG. 2. In some embodiments, the one or more components of the imaging system 200 configured to acquire X-ray radiation may be considered an X-ray imaging subsystem (e.g., the X-ray source 104, the detector array 108, etc.) of the overall imaging system 200, which may be a computing system further configured to interface with a user and perform a variety of computational processes (e.g., imaging or non-imaging). Accordingly, other components (e.g., the computing device 216, etc.) of the imaging system 200 may be communicably coupled to the X-ray imaging subsystem.

In some embodiments, the computing device 216 may store the data in a storage device or mass storage 218, either included in the computing device 216 (in such examples, the computing device 216 may be referred to as a controller) or a separate device communicably coupled to the computing device 216 (in such examples, the computing device 216 may be referred to as a processor). The storage device 218 may include removable media and/or built-in devices. Specifically, the storage device 218 may include one or more physical, non-transitory devices configured to hold data and/or instructions executable by the computing device 216 to implement the herein described methods. Accordingly, when such methods are implemented, a state of the storage device 218 may be transformed (for example, to hold different, or altered, data). The storage device 218, for example, may include magnetoresistive random-access memory (MRAM), a hard disk drive, a floppy disk drive, a tape drive, a compact disk-read/write (CD-R/W) drive, a Digital Versatile Disc (DVD) drive, a high-definition DVD (HD-DVD) drive, a Blu-Ray drive, a flash drive, and/or a solid-state storage drive. It will be appreciated that the storage device 218 may be a non-transitory storage medium.

Additionally, the computing device 216 may provide commands and parameters to one or more of the DAS 214, the X-ray controller 210, and the gantry motor controller 212 for controlling system operations such as data acquisition and/or processing. In certain embodiments, the computing device 216 controls system operations based on operator input, e.g., via a user interface 234. The computing device 216 receives the operator input, for example, including commands and/or scanning parameters via an operator console 220 operatively coupled to the computing device 216. The operator console 220 may include a physical keyboard, mouse, touchpad, and/or touchscreen to allow the operator to specify the commands and/or scanning parameters.

In some embodiments, the computing device 216 may include, or be coupled to, one or more multicore CPUs or a plurality of general-purpose GPUs (GPGPUs) 236, where the plurality of GPGPUs 236 may be configured to execute instructions stored in non-transitory memory of the computing device 216 (e.g., the storage device 218) via highly parallelized data and computation streams.

Although FIG. 2 illustrates only one operator console 220, more than one operator console 220 may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 may either include, or may be coupled to, a picture archiving and communications system (PACS) 224. In an exemplary implementation, the PACS 224 may further be coupled to a remote system such as radiological information systems (e.g., RIS), electronic health or medical records and/or hospital information systems (e.g., EHR/HIS), and/or to an internal or external network (not shown) to allow operators at different locations to supply commands and parameters and/or gain access to the image data.

The computing device 216 may use the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. For example, one embodiment may use computing resources in a "cloud" network cluster for the image reconstructor 230.

In one embodiment, the image reconstructor 230 may store the images reconstructed in the storage device 218, either via the computing device 216 as shown in FIG. 2 or via a direct connection (not shown). Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods or processes (such as the method described below with reference to FIG. 6) described further herein may be stored as executable instructions in non-transitory memory on a computing device (or controller), or in communication with a computing device (or processor), in the imaging system 200. In one embodiment, the image reconstructor 230 may include such executable instructions in non-transitory memory, and may apply the methods described herein to reconstruct an image from scanning data. In another embodiment, the computing device 216 may include the instructions in non-transitory memory, and may apply the methods described herein, at least in part, to a reconstructed image after receiving the reconstructed image from the image reconstructor 230. In yet another embodiment, the methods and processes described herein may be distributed across the image reconstructor 230 and the computing device 216.

In operation, the computing device 216 may acquire imaging data and other medical data, which may be translated for display to a user (e.g., a medical professional) via the user interface 234, for example, on the display device 232. As an example, the medical data may be transformed into and displayed at the display device 232 as a user-facing graphical and/or textual format, which may be standardized across all implementations of the imaging system 200 or may be particular to a given facility, department, profession, or individual user. As another example, the imaging data (e.g., three-dimensional (3D) volumetric data sets, two-dimensional (2D) imaging slices, etc.) may be used to generate one or more images at the computing device 216, which may then be displayed to the operator or user at the display device 232. As such, the display device 232 may allow the operator to evaluate the imaged anatomy. The display device 232 may also allow the operator to select a volume of interest (VOI) and/or request patient information, for example, via a graphical user interface (GUI) for a subsequent scan or processing.

Image reconstruction algorithms for CT imaging systems may be structured around discretization of tomographic operators or projectors. CT imaging data may be acquired in the form of a plurality of line integral measurements corresponding to a distribution of attenuation coefficients of an object of interest. Specifically, X-ray imaging systems, such as CT imaging systems, may acquire measurements collected at a set of lines belonging to a geometric object, such as a cone. For example, an X-ray beam may be divergent from a focal point of an X-ray source (e.g., an X-ray tube) and may be shaped as a cone by a collimation window upon exiting the X-ray source. After passing through an object of interest, the divergent X-ray beam cone may then be entirely captured by an X-ray detector. Accordingly, an overall shape and configuration of the X-ray detector may define a surface of intersection with the divergent X-ray beam cone. An image formed at the surface of intersection may be referred to as a projection (e.g., the plurality of line integral measurements). The surface of intersection may take on a number of geometries (e.g., curved, flat, etc.), but in principle may be arbitrary. In some examples, a plurality of projections may be acquired at a plurality of positions of the X-ray imaging system during acquisition of the CT imaging data.

The tomographic operator may be selected to encode a geometric representation of a plurality of lines of integration (also referred to as rays, in some examples) along which the plurality of line integral measurements is taken. However, it will be appreciated that additional or alternative factors may be considered in obtaining the plurality of line integral measurements, such as depth-dependent resolution distortion, hardening of the X-ray spectrum along the rays (e.g., via selective attenuation of low-energy photons), and/or considerations specific to emission tomographic modalities, where the integral measurements may represent cumulated radioactive activity along a given ray.

In practice a finite number I of projections $p_i$ may be collected, where the finite number I may be a product of a finite number of positions and a finite number of measurement points (also referred to herein as bins) on the X-ray detector. A distribution of interest (e.g., the distribution of the attenuation coefficients of the object of interest) may also be sampled (e.g., computed) at a finite number of points to obtain a finite number J of distribution samples $f_j$. However, in contrast to the projections $p_i$, the finite number J of distribution samples $f_j$ and respective locations thereof at which the distribution of interest is computed may be arbitrary (as the true distribution of interest is continuous). As used herein, "continuous" when referring to a function, parameter, or other measure may mean defined everywhere (e.g., at an infinite set of locations) and in opposition to "discrete, which when referring to a function, parameter, or other measure herein may mean defined at a finite set of locations.

Without loss of generality, the case of a single position in the X-ray imaging system may be considered. Discretization of the projector may couple the finite number I of projections $p_i$ to the finite number J of distribution samples $f_j$ by decomposing continuous quantities as a sum of basis objects scaled by respective sample values (e.g., a basis set expansion).

Discretization may be viewed from two perspectives: that of the X-ray detector and that of the distribution of interest. Regarding the X-ray detector, and as described above, detection may occur at the finite number of bins, each bin corresponding to a subset of an overall volume of interest. Since each of the bins may have a relatively small size, the projection $p_i$ measured at an ith bin may be a line integral over an ith line, or ray, originating at a location $u_i$ set as a center of the ith bin. A numerical integration algorithm may decompose the ith line into S segments, where each segment may have a length $l_s$ and a distribution value $f_s$, such that:

$$p_i = \int_{-\infty}^{+\infty} f(l) dl = \sum_{s=1}^{S} f_s l_s \qquad (3)$$

where f(l) is the (continuous) distribution of interest along the ith line.

Regarding the distribution of interest, the finite number J of distribution samples, or grid samples, $f_j$ (e.g., a discrete set) may be defined on a three-dimensional (3D) Cartesian grid of J regularly spaced locations $x_j$ (however, in other examples, the locations $x_j$ may be variably spaced). Accordingly, with a divergent X-ray beam cone, there may be close to no ray having a same direction as a given alignment of the locations $x_j$. Specifically, on Cartesian grids, the locations $x_j$ may be aligned along at least three directions (e.g., a degree of freedom for each dimension as well as additional possible lines, such as at 45° angles within a plane, etc.); however, a divergent set of rays may cover all directions between an X-ray source and a detector, such that no alignment with the locations $x_j$ may be achieved. To couple the grid samples $f_j$ located at the locations $x_j$ to the distribution values $f_s$, modeling of the distribution of interest may be extended by considering each grid sample $x_j$ as a center of a voxel of uniform intensity $f_j$ (e.g., corresponding to the distribution sample $f_j$). The voxel may be shaped as a geometrical object, such as a square cuboid (where one dimension may be the same or different from two remaining, equal dimensions which define planes of square pixels). Numerical integration may proceed by defining a plurality of segments $l_{ij}$ as an intersection between an ith ray and a jth voxel, yielding:

$$p_i = \sum_{j=1}^{J} f_j l_{ij} \qquad (4)$$

In the algebraic formulation, a vector p of all projections $p_i$ may be represented as a product of an operator R with a vector f of all distribution samples $f_j$ such that p=Rf. Accordingly, R may be represented as a matrix of I rows and J columns storing coefficients $r_{1 \leq i \leq I, 1 \leq j \leq J}$ and may be referred to as a projector or forward projector. The matrix-vector product of the forward projection operation may be written as:

$$p_i = \sum_{j=1}^{J} r_{ij} f_j \qquad (2)$$

Since the coefficients $r_{ij}$ are real, the adjoint operator of R is the transpose matrix and is referred to as a backprojector. The matrix-vector product of the backward projection operation may be written as:

$$f_j = \sum_{i=1}^{I} r_{ij} p_i \qquad (1)$$

One class of discretization model which may be employed includes the so-called ray-driven models. Ray-driven models may utilize a geometric representation, where a plurality of lines formed by the I rays originating at the plurality of locations u, and crossing the focal point of the X-ray source.

Ray-driven models may employ one of a number of numerical integration schemes known as ray-driven multilinear interpolation. As an example, a cubic sampling grid may be used with a sampling rate of 1 along each grid axis. An integration length may also be set to 1, such that fixed-length segments may be obtained. As such, equation (4) may simplify to:

$$p_i = \sum_{s=1}^{S} f_s \qquad (5)$$

where distribution values $f_s$ may be regularly spaced over an ith ray. Accordingly, the distribution values $f_s$ may be linearly interpolated from two closest samples in the direction of each grid axis. It should be noted that no shape is assumed for the voxel in ray-driven models. Further, as multilinear interpolation may be separable, d linear interpolations may be formulated for a sampling grid having d dimensions.

Joseph's method is one simplification of ray-driven multilinear interpolation. In Joseph's method, numerical integration still relies on fixed-length segments; however, larger-sized segments may be used. To define the larger-sized segments, the distribution of interest may be cast as a set of parallel hyperplanes orthogonal to one axis of the sampling grid, where the set of parallel hyperplanes may be regularly spaced along the grid axis with spacing $\delta$ (e.g., $\delta=1$). A length $l_{\theta_i}$ between two consecutive hyperplanes along an ith line (ray) may also be constant, depending upon an angle $\theta_i$ between the ith line and the grid axis. The grid axis may be selected to yield an angle $\theta_i$ such that $\delta \leq l_{\theta_i} \leq \delta \sqrt{2}$.

Accordingly, locations of the distribution values $f_s$ may coincide with locations of the distribution samples $f_j$ along the grid axis orthogonal to the hyperplanes. For each other grid axis, separable linear interpolation may be employed. Thus, for a d-dimensional grid, Joseph's method may utilize d-1 linear interpolations (e.g., one less than ray-driven multilinear interpolation as discussed above). Joseph's model may be well-suited for CT imaging, for example, while redundancy resulting from ray-driven multilinear interpolation may be desirable for graphics and display.

One desirable property of ray-driven models is to leverage 100% of the bins (e.g., for every ith bin) being computed from (e.g., during reprojection), or partitioned over (e.g., during backprojection), the sampling grid, which may be mathematically represented as follows:

$$\forall i, \sum_{j=1}^{J} r_{ij} = 1 \qquad (6)$$

However, there may be no guarantee that the voxels are similarly 100% accounted for. Mathematically, this may be represented as:

$$\exists j, \sum_{i=1}^{I} r_{ij} \neq 1 \qquad (7)$$

Depending upon the value of the number I, the voxels may be under- or oversampled (resulting in holes or redundancies, respectively).

To account for the voxels, a voxel-driven model may be used. In contrast to ray-driven approaches to discretization (as discussed in detail above), voxel-driven models leverage 100% contribution of each distribution sample $f_j$ to the X-ray detector. Voxel-driven models may thus be characterized by how a determination of contributions of each of the distribution samples $f_j$ to the measurements (bins) is made.

In voxel-driven models, linear interpolation accounts for a line integral passing through each jth distribution sample $f_j$, e.g., integration along a line that joins the focal point of the X-ray source to a jth grid sample $x_j$. An intersection of the line with the X-ray detector may be defined by a continuous function $u(x)$, which may not necessarily correspond to the location $u_i$ at the center of the ith bin, and instead may more generally correspond with a location $u(x_j)$ in the ith bin (accordingly, the line may be referred to herein as the line $u(x_j)$, as the line may be defined with respect to the X-ray source by the location $u(x_j)$ at the detector). Since the line $u(x_j)$ may be the only line which passes through the jth grid sample $x_j$ and the focal point of the X-ray source for a given position of the X-ray source and the X-ray detector, the distribution sample $f_j$ may contribute 100% to the line $u(x_j)$ (e.g., the distribution sample $f_j$ may contribute 100% to a measurement made at the location $u(x_j)$ over the line defined by joining of the X-ray source to the location $u(x_j)$). Contributions to neighboring locations $u_i$ may then be determined by partitioning the distribution sample $f_j$ according to linear interpolation coefficients deduced from the line $u(x_j)$ and two nearest neighboring locations $u_i$. Accordingly, because a given line $u(x_j)$ may be modeled as interacting with multiple locations $u_i$ in such a way that a given location $u_i$ is also modeled as interacting with multiple lines $u(x_j)$, asymmetric linear dependencies may exist in voxel-driven models (as encoded by the operator R).

A geometrical model may be selected to describe the plurality of voxels. For example, and as described above, each of the plurality of voxels may be shaped as a square cuboid of uniform intensity $f_j$. In voxel-driven models, the projection, or footprint, of the voxel on the X-ray detector may be determined by the shape of each voxel, which for square cuboids is a trapezoid having a width which varies as a function of an angle of projection. A geometrical model may also be selected for the X-ray detector. For example, the X-ray detector may be partitioned into uniform bins. The (discretization) coefficient $r_{ij}$ may therefore be interpreted as a quantification of an interaction between a footprint of a given voxel at location $x_j$ and a support originating from an ith bin of the X-ray detector. Such interactions form the so-called distance-driven model.

Referring now to FIG. 3, a schematic diagram 300 illustrating interactions in an exemplary distance-driven model is shown. The exemplary distance-driven model, being a voxel-driven model based on a geometric representation of the lines of integration, may consider two sets of lines: (i) a plurality of origin lines 302 extending from a focal point 324 of an X-ray source to respective edges 306 of a plurality of voxels 304 (e.g., at a dashed line 308); and (ii) a plurality of destination lines 312 extending from the focal point 324 of the X-ray source to respective edges 316 of a plurality of bins 314 of an X-ray detector (full extension of the plurality of destination lines 312 to the focal point 324 of the X-ray source not shown for clarity). A projection axis 322 may serve as a reference for a relative location of the plurality of voxels 304 and the plurality of bins 314 by defining sets of line segments (e.g., of lines 302, 312; also referred to herein as supports), lengths of which may weight values of respective projections (e.g., footprints) of the plurality of voxels 304 and the plurality of bins 314. Further, because the plurality of voxels 304 and the plurality of bins 314 may be cast as relatively simple geometric objects, projections along the projection axis 322 may be completely described from a geometric perspective. However, the plurality of origin lines 302 may have a different density of information than the plurality of destination lines 312 as a result of the two sets of lines 302, 312 being based off of different sampling schemes (the plurality of voxels 304 and the plurality of bins 314, respectively). Accordingly, interpolation schemes may be necessary to unify the two projections, removing asymmetric linear dependencies therebetween by accounting for the different densities of information.

In contrast with ray-driven models, in voxel-driven models, 100% of the voxels (e.g., for every jth voxel) may be detected and shared over the bins, which may be mathematically represented as:

$$\forall j, \sum_{i=1}^{I} r_{ij} = 1 \qquad (8)$$

However, and again in contrast with ray-driven models, there may be no guarantee in voxel-driven models that the bins are similarly 100% accounted for. Mathematically, this may be represented as:

$$\exists i, \sum_{j=1}^{J} r_{ij} \neq 1 \qquad (9)$$

Depending upon the value of the number J, the bins may be under- or oversampled (resulting in holes or redundancies, respectively).

Due to poor bin sampling, linear interpolation in voxel-driven models may be an inaccurate projector model and ill-suited to reprojection and iterative image reconstruction (cf. equation (2)). However, 100% voxel sampling may suit voxel-driven models for backprojection and analytical image reconstruction (the latter employing one backprojection and no reprojection). Further, as opposed to partitioning of a contribution of the distribution sample $f_j$ at the grid sample $x_j$ over neighboring bins, linear interpolation in voxel-driven models may be interpreted as summing of a detector measurement along the line $u(x_j)$ to the distribution sample $f_j$ (under the assumption that all detector measurements form the continuous function $u(x)$, from which the detector measurement along the line $u(x_j)$ may be determined via the linear interpolation).

The distance-driven model may achieve both conditions of 100% voxel sampling (e.g., equation (8)) and 100% bin sampling (as the interaction is chosen to verify equation (6)). Accordingly, the distance-driven model may be equally suited for reprojection and backprojection and may therefore be successfully utilized in iterative image reconstruction algorithms. However, precision imaging and massively parallel implementation may be precluded by omission of the continuous function u(x), such that the distance-driven model may rely instead on ordered determination of the locations of intersection via sequential scanning of the (sampling) grid axes According to the embodiments described herein, a one-dimensional resampling transform may provide a more general framework for separable interpolation. Since one-dimensional resampling transforms may not assume a multidimensional geometrical shape, one-dimensional subsets of samples may instead be considered, each sample having a sampling location and, instead of a geometrical shape, a one-dimensional basis function.

In the context of image transformations, resampling transforms may be employed as translations, rotations, and magnifications. Such resampling transforms are special cases of homographic transforms. Accordingly, homographic transforms may be ideally suited for resampling of projections obtained in a flat-panel detector-based cone-beam tomographic geometry, as such projections may be related as magnifications and rotations. Further, the invertibility of all homographic transforms may be desirable for resampling.

A homographic resampling transforms may be viewed as a change of variable. For example, a homographic resampling transform h may replace a variable x with a variable u, e.g., u=h(x). Reciprocally, the variable u may be replaced with the variable x via x=h$^{-1}$(u).

Herein, notation used in the context of resampling transforms may be simplified by employing u(x) and x(u) such that x(u(x))=x and u(x(u))=u, respectively. Accordingly, the projection operation, being linear, may be decomposed into summing a projection p(u) computed as a resampling of a restriction of the distribution f to one axis, e.g., x for f(x), via the homographic resampling transform u(x) (such that p∘u=f, e.g., p(u(x))=f(x)).

The (real-valued) function u(x) for x ∈]−∞, +∞[ is a one-dimensional homography, defined by:

$$u(x) = \frac{h_{11}x + h_{12}}{h_{21}x + h_{22}} \qquad (10)$$

where $h_{11}$, $h_{12}$, $h_{21}$, and $h_{22}$ are elements of a transformation matrix H, e.g., $$H = \begin{pmatrix} h_{11} & h_{12} \\ h_{21} & h_{22} \end{pmatrix} \qquad (11)$$

Using an intermediate coordinate s(x)=$h_{21}$x+$h_{22}$, a real-valued matrix relation may be obtained with homogeneous coordinates su(x)=s(x)u(x) and s(x) as:

$$\begin{pmatrix} su \\ s \end{pmatrix} = H \begin{pmatrix} x \\ 1 \end{pmatrix} \qquad (12)$$

Considering a matrix $H_\lambda$=λH, where λ is a real, non-zero scalar value, the same resampling may be obtained:

$$u(x) = \frac{\lambda h_{11}x + \lambda h_{12}}{\lambda h_{21}x + \lambda h_{22}} = \frac{h_{11}x + h_{12}}{h_{21}x + h_{22}} \qquad (13)$$

(however, in the case of $H_{80}$, a different intermediate coordinate $s_\lambda$(x)=λs(x) may be employed). Since λ is chosen to be non-zero, the transformation matrix H may be assumed invertible and therefore suitable for resampling.

Notably, and without loss of generality, the transformation matrix H may further be selected to be a unimodular matrix, e.g., such that $h_{11}h_{22}$−$h_{12}h_{21}$=1 or |H|=1.

Since the transformation matrix H is invertible, inverse resampling (e.g., the function x(u)) may be associated to the matrix H$^{-1}$, which may be given as:

$$H^{-1} = \begin{pmatrix} h_{22} & -h_{12} \\ -h_{21} & h_{11} \end{pmatrix} \qquad (14)$$

since the transformation matrix H is a 2×2 matrix. Similar to the intermediate coordinate s(x) defined for u(x), an intermediate coordinate t(u)=−$h_{21}$u+$h_{11}$, such that (and analogous to the discussion above):

$$\begin{pmatrix} tx \\ t \end{pmatrix} = H^{-1} \begin{pmatrix} u \\ 1 \end{pmatrix} \qquad (15)$$

(accordingly, it follows that tx(u)=t(u)x(u)).

Derivatives u'(x) and x'(u) may provide a local approximation of the homography and may be given as:

$$u'(x) = \frac{1}{s^2(x)} \qquad (16)$$

and $$x'(u) = \frac{1}{t^2(u)} \qquad (17)$$

respectively. Accordingly, a magnification factor in x may be s$^2$(x) and an inverse magnification factor in u may be [t$^2$(u)]$^{-1}$. Further, in the case that $h_{21}$=0, |H|=$h_{11}h_{22}$=1 and the magnification factors in x and u are constant, e.g., $$s^2(x) = h_{22}^2 = \frac{h_{22}}{h_{11}} = \frac{1}{h_{11}^2} = \frac{1}{t^2(u)} \qquad (18)$$

In the flat-panel detector-based cone-beam tomographic geometry, a relationship between a point (x, y, z) in space and a projection (u(x, y, z), v(x, y, z)) thereof over a detection plane may accordingly be described with homogeneous coordinates s(x, y, z), su(x, y, z)=s(x, y, z)u(x, y, z), and sv(x, y, z)=s(x, y, z)v(x, y, z) through a 3×4 projection matrix P as:

$$\begin{pmatrix} su \\ sv \\ s \end{pmatrix} = P \begin{pmatrix} x \\ y \\ z \\ 1 \end{pmatrix} \qquad (19)$$

Such a formalism may be adapted to the interpolation schemes discussed above. For example, ray-driven models may loop through the lines (rays) to obtain an equation of an ith line in space via:

$$\begin{pmatrix} su_i \\ sv_i \\ s \end{pmatrix} = P \begin{pmatrix} x \\ y \\ z \\ 1 \end{pmatrix} \quad (20)$$

Similarly, voxel-driven models may loop through the voxels to directly compute a projection $(u(x_j, y_j, z_j), v(x_j, y_j, z_j))$ of a voxel $(x_j, y_j, z_j)$, e.g., as:

$$\begin{pmatrix} su \\ sv \\ s \end{pmatrix} = P \begin{pmatrix} x_j \\ y_j \\ z_j \\ 1 \end{pmatrix} \quad (21)$$

By instead employing the one-dimensional resampling transform, the projection operation may be decomposed into a linear combination of transforms, each transform relating one free variable in space (e.g., x) and one free variable over a surface of the X-ray detector (e.g., u). For example, resampling (e.g., via u(x) formalism, as described above) may be represented as:

$$\begin{pmatrix} su \\ sv_i \\ s \end{pmatrix} = P \begin{pmatrix} x \\ y_j \\ z_j \\ 1 \end{pmatrix} \quad (22)$$

Accordingly, for any pair (i, j), there may be six possible resampling transforms: u(x), v(x), u(y), v(y), u(z), and v(z). The projection decomposition may involve looping over (i, j) and selecting one of the six resampling transforms for each loop. A resulting subset of resampling transforms may be selected so as to have invertible homographies. For example, a looping scheme in a voxel-driven model may include first looping through j and first fixing $z=z_j$ and then $y=y_j$, and then for all i splitting the interpolation between u(x) and v(x) (which are independent and separable from one another). Axes x, y, and z may be swapped as desired in the preceding looping scheme for looping voxels along the respective axes x, y, and z. If i is swapped with j, then looping for a ray-driven model may be obtained.

Thus, without loss of generality, the following discussion will refer to u(x) and x(u) as exemplary. Accordingly, of the plurality of voxels (indexed with j and having a size equal to the finite number J), a subset lying on the axis x may be indexed with 1 and have a size equal to a finite number L. Likewise, of the plurality of bins (indexed with i and having a size equal to the finite number I), a subset lying on an axis u may be indexed with k and have a size equal to a finite number K. As such, the index k may subsample the index i and the index 1 may subsample the index j, such that $r_{lk} = r_{ij}$ according to u(x).

In image reconstruction, forward projection (reprojection) may be described as mapping a volume over a surface and backprojection may be described as mapping the surface back over the volume. Such mappings may be decomposed into a sum of simpler, separable mappings, such that a given image reconstruction model may be described as a projection of a single line of a volume over a line of the projection (surface) and vice versa.

For example, and as discussed below with reference to FIGS. 4A and 4B, the homography-based model of the present disclosure may be fully described with a single (one-dimensional) homographic resampling transform over a single axis. Accordingly, a set of one-dimensional homographic resampling transforms may form a symmetric projector/backprojector pair (e.g., as matrices of voxel-bin interactions at the surface), which may be leveraged in an image reconstruction algorithm.

Figure 4A:
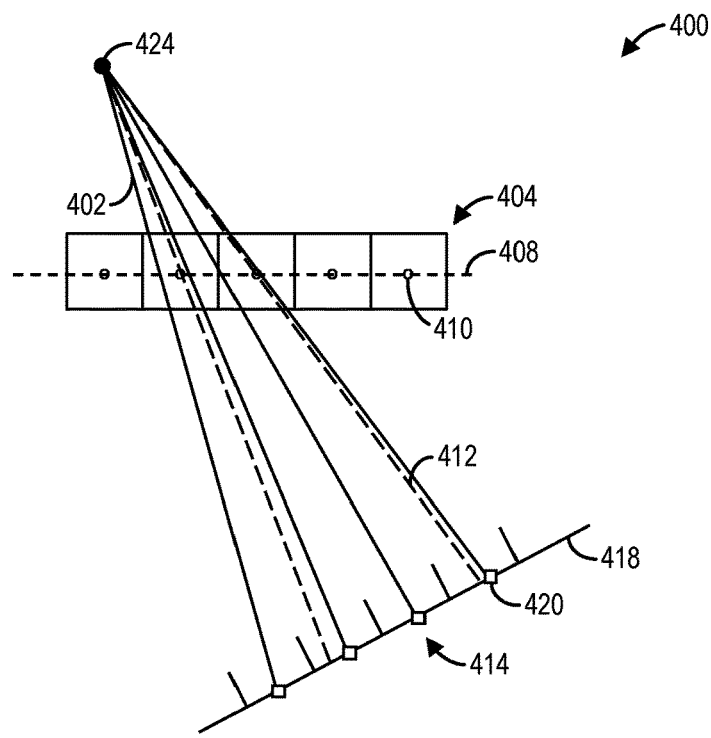
FIG. 4A shows a schematic diagram of an exemplary flat-panel detector-based cone-beam tomographic geometry, according to an embodiment.
Figure 4B:
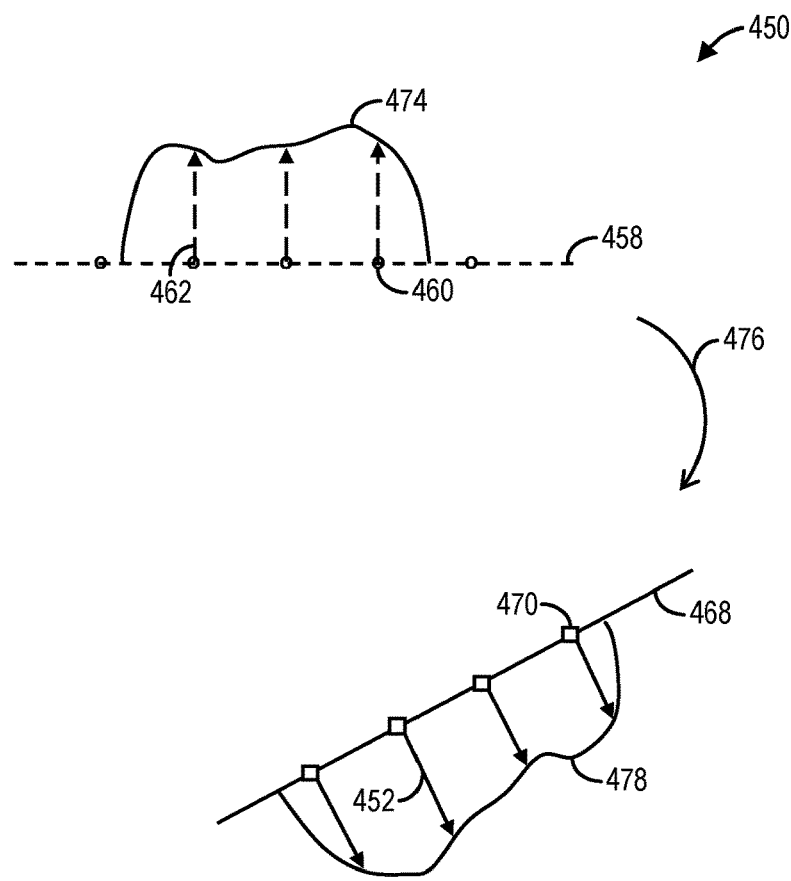
FIG. 4B shows a schematic representation of an exemplary one-dimensional homographic resampling transform, according to an embodiment.

Referring now to FIG. 4A, a schematic diagram 400 illustrating an exemplary flat-panel detector-based cone-beam tomographic geometry is shown. Two sets of lines may geometrically represent lines of integration being sampled: (i) a plurality of dashed lines 402 extending from a focal point 424 of an X-ray source to respective centers 410 of a subset of voxels 404 (e.g., along a dashed line 408 parallel with the axis x); and (ii) a plurality of lines 412 extending from the focal point 424 of the X-ray source to respective centers 420 of a subset of bins 414 (e.g., along a line 418 on an X-ray detector, the surface 418 parallel with the axis u). However, in contrast to the geometry-based perspective described with reference to FIG. 3, only a single, one-dimensional point (e.g., of the centers 410, 420) need be considered for each of the sampled lines of integration in a homography-based perspective (instead of two-dimensional, projected faces of voxels and bins). Specifically, each of the one-dimensional points respectively corresponding to the lines of integration sampled at the centers 410 of the subset of voxels 404 and the centers 420 of the subset of bins 414 may be mapped to a single, continuous function via a one-dimensional homographic resampling transform (as described below with reference to FIG. 4B). Accordingly, in the homography-based perspective, the geometric representation of the lines of integration (e.g., the lines 402, 412) may not be considered at all.

Referring now to FIG. 4B, a schematic diagram 450 illustrating an exemplary one-dimensional homographic resampling transform 476 is shown. A plurality of points 460 (e.g., centers of a subset of voxels) may represent respective locations of a plurality of samples 462 of a distribution 474 along an axis 458. Similarly, a plurality of points 470 (e.g., centers of a subset of bins of an X-ray detector) may represent respective locations of a plurality of samples 452 of a distribution 478 along an axis 468. As shown, the distribution 474 may be mapped (e.g., transformed) into the distribution 478 via the one-dimensional homographic resampling transform 476. In this way, a one-dimensional homographic resampling transform may entirely supplant geometric representations of lines of integration in an image reconstruction algorithm.

To resample a single, continuous function g at an arbitrary location x from M samples $g_m$ at fixed, known locations $x_m$ (referred to as "source samples"), a basis function β(x, m) defined for $x \in ]-\infty, +\infty[$ may be introduced for each $x_m$ to describe the function g with respect to the location $x_m$. Accordingly, a continuous approximation of g may be given by a finite sum of M basis functions:

$$g(x) = \Sigma_m g_m \beta(x, m) \quad (23)$$

In some examples, each basis function β(x, m) may be efficiently represented as $β(x, m) = β(x - x_m)$.

In a linear interpolation scheme, the basis function β(x, m) may be a basis function $β_1(x)$ defined as:

$$\beta_1(x) = \begin{cases} 1 - |x|, & |x| \le 1 \\ 0, & |x| > 1 \end{cases} \quad (24)$$

In a nearest-neighbor interpolation scheme, the basis function $\beta(x, m)$ may be a basis function $\beta_0(x)$ defined as:

$$\beta_0(x) = \begin{cases} 1, & |x| < \frac{1}{2} \\ \frac{1}{2}, & |x| = \frac{1}{2} \\ 0, & |x| > \frac{1}{2} \end{cases} \quad (25)$$

Numbered indices "0" and "1" index the basis functions according to a family of functions referred to as the B-spline of order n. Specifically, interpolation basis functions of order n>0 may be defined recursively based on the B-spline of order n as:

$$\beta_n = \beta_{n-1} * \beta_0 \quad (26)$$

where "*" denotes convolution. For example:

$$\beta_1 = \beta_0 * \beta_0 \quad (27)$$

Further, each basis function in the B-spline of order n may verify:

$$\beta_n(x) = \beta_n(-x) \quad (28)$$

In the continuous domain, homographies $u(x)$ and $x(u)$ may describe the same relationship between a given line (subset) of voxels of the distribution f and a given line (subset) of bins of the projection p such that $p(u)=f(x)$. Though in a geometric perspective, the lines of voxels and bins are at different locations in space, functions $u(x)$ and $x(u)$ map $f(x)$ and $p(u)$ to the same axis by substituting one variable with the other (e.g., x with u or vice versa). Specifically, the function $u(x)$ maps both of the functions $f(x)$ and $p(u)$ along the axis u and the function $x(u)$ maps both of the functions $f(x)$ and $p(u)$ along the axis x. However, since sampling along the axis x may differ from sampling along the axis u, equivalent discretization may not be guaranteed. Along the axis x, L points (e.g., centers of the subset of voxels along the axis x, as described above with reference to FIG. 4) may be equally spaced with spacing $\delta_x$. Along the axis u, K points (e.g., centers of the subset of bins along the axis u, as described above with reference to FIG. 4) may be equally spaced with spacing $\delta_u$.

Accordingly, a basis function $\beta_{n,\delta}(x)$ may be introduced to explicitly account for spacing $\delta$, which may be variously represented as:

$$\beta_{n,\delta}(x) = \beta_{n,1}\left(\frac{x}{\delta}\right) = \beta_n\left(\frac{x}{\delta}\right) \quad (29)$$

Employing a basis set expansion with the basis function $\beta_{n,\delta}(x)$, one of two continuous models may be obtained:

$$p(u) = f \circ x(u) = f(x) = \Sigma_k f_k \beta_{\delta_x}(x) \quad (30)$$

and $$f(x) = p \circ u(x) = p(u) = \Sigma_l p_l \beta_{\delta_u}(u) \quad (31)$$

for the projection p and the distribution f, respectively (where a notation of $\beta_{n,\delta}(x)$ is simplified to $\beta_{\delta_x}(x)$ for the spacing $\delta_x$ and $\beta_{\delta_u}(u)$ for the spacing $\delta_u$).

The spacing $\delta$ may be understood as an inverse of a sampling rate $\delta^{-1}$. Accordingly, a change of the spacing $\delta$ may result in a change of the sampling rate $\delta^{-1}$ and may be quantified as a magnification, e.g., $\delta_x/\delta_u$. In some examples, a continuous model (e.g., either equation (29) or (30)) may be selected based on whichever sampling rate (e.g., $1/\delta_x$ or $1/\delta_u$) is higher.

Figure 5:
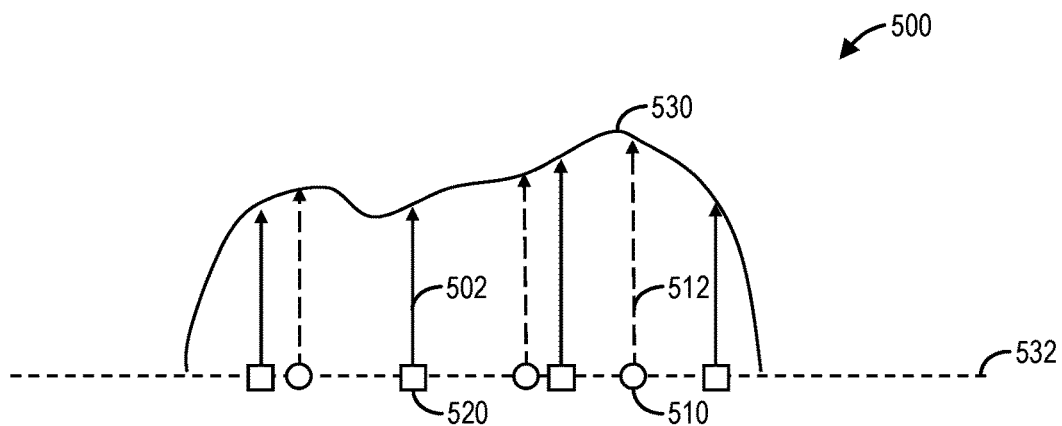
FIG. 5 shows a schematic representation of a basis set approximation of a continuous function resampled with the exemplary one-dimensional homographic resampling transform, according to an embodiment.

Referring now to FIG. 5, a schematic diagram 500 illustrating a basis set approximation of a continuous function resampled with an exemplary one-dimensional homographic resampling transform, such as the exemplary one-dimensional homographic resampling transform 476 described above with reference to FIG. 4B, is shown. From a resampling perspective, a function $h(x)$ exists such that $p(u)=f \circ h(x)$. Accordingly, the function $f(x)$ (e.g., the distribution f) and the function $p(u)$ (e.g., the projection p) may be the same function, but at different sampling locations, e.g., $x_l$ for the function $f(x)$ and $u_k$ for the function $p(u)$, and along different axes. However, the functions $f(x)$ and $p(u)$ may be placed along a single axis, since locations $x_l$ may be transformed into locations $h(x_l)$ via the function $h(x)$, which may be placed onto the same axis as locations $u_k$. The function $p(u)$ may then be modeled as a sum of basis functions defined with respect to a set $\{u_{1 \leq k \leq K}, h(x_{1 \leq l \leq L})\}$ of all locations over the same axis. Interpolation weights for the modeling may then be obtained by computing values of the basis functions at selected locations. As the basis functions may be globally continuous, computation thereof may be performed independently at any point, at any time, and thus in parallel. In this way, algorithms leveraging the one-dimensional homographic resampling transform may be easily adapted to a massively parallel computing architecture.

As shown in the schematic diagram 500, exemplary locations 510 may represent the locations $h(x_l)$ and exemplary locations 520 may represent the locations $u_k$. The locations 510, 520 are accordingly plotted along a same axis 532 and respectively mapped 512, 522 to a same function 530, where the function 530 may represent the continuous approximation of $p(u)=f \circ h(x)$ as a sum of basis functions. The single-axis representation of the one-dimensional homographic resampling transform described with reference to FIG. 5 may be compared to the representation described with reference to FIG. 4B, which shows the function 474 sampled along the axis 458 being transformed 476 to the function 478 sampled along the axis 468. Note in FIG. 4B that the functions 474, 478 are depicted with a similar shape, illustrating an equivalence thereof. In this way, the geometric representation illustrated at FIG. 3 may be replaced by a single function along a single axis (shown at FIG. 5 as the axis 532 of a detector coordinate u, but using an axis of a sampling coordinate x provides an equivalent framework).

It should be noted that the basis set expansions described above may be intermediate in nature, as a resulting model may be constructed from the (discrete) set of coefficients $r_{kl}$. As an example, in voxel-driven models, one basis function $\beta_{n,\delta}(x)$ may be set per voxel location $x_l$ from which samples may be computed at positions $x(u_k)$, yielding the following coefficients:

$$r_{kl} = \beta_{n,\delta_x}(x(u_k) - x_l) \quad (32)$$

As another example, in ray-driven models, one basis function $\delta_{n,\delta}(x)$ may be set per bin location $u_k$ from which samples may be computed at positions $u(x_l)$, yielding the following coefficients:

$$r_{kl} = \delta_{n,\delta_u}(u(x_l) - u_k) \quad (33)$$

Of course, adapting homography-driven models to ray-driven and voxel-driven models may not remedy any limitations thereof. However, a homographic representation may advantageously provide valuable insight into such limitations from an alternative perspective. For example, in a homographic representation, ray-driven and voxel-driven models may select one sampling axis (e.g., the axis x or the axis u) adequate for a correspondingly one-sided perspective of image reconstruction. However, and as the homographic representation elucidates, an analogous model may be induced over the other axis. For example, the function p(u) may be represented as both:

$$p(u)=f \circ x(u)=f(x)=\Sigma_i f_i \beta_{\delta_x}(x)=\Sigma_i f_i \beta_{\delta_x} \circ x(u) \quad (34)$$

and $$p(u)=\Sigma_k p_k \beta_{\delta_{u(x)}}(u) \quad (35)$$

(cf. equations (30) and (31), respectively).

Because a homography may act locally as a magnification (as discussed above), on the axis x, the basis function $\beta_{\delta_x}(x)$ may be represented as:

$$\beta_{\delta_x}(x)=\beta_{\delta_x} \circ x(u) \quad (36)$$

with the fixed spacing $\delta_x$. However, on the axis u, the induced basis functions $\beta_{\delta_{u(x)}}(u)$ may have continuously variable spacing $\delta_{u(x)}$, e.g., $$\delta_{u(x)} = \frac{\delta_x}{x'(u)} \quad (37)$$

Since the continuously variable spacing $\delta_{u(x)}$ may not coincide with measurement $p_l$ (which may have the fixed spacing $\delta_u$ imposed by detector design), the basis functions $\beta_{\delta_{u(x)}}(u)$ may not provide an adequate resampling expansion of the function p(u) using uniformly-spaced measurements $p_l$; however, an adequate resampling expansion may be provided by the basis functions $\beta_{\delta_{u(x)}}(u)$ for the function p(u) using the samples $f_l$. Reciprocally, the basis functions $\beta_{\delta_{u(x)}}(u)$ may not provide an adequate resampling expansion for a function f(x) using the samples $f_k$; however, an adequate resampling expansion may be provided by the basis functions $\beta_{\delta_{u(x)}}(u)$ for the function f(x) using the samples $p_k$.

Accordingly, when resampling a given function, homography-driven models may be adequate resampling expansions when used for destination-driven resampling. Specifically, the resampling expansion may be selected for an axis describing uniformly-spaced, known samples (the source samples, as described above), and resampling locations (referred to as "destinations") may be given by the resampling transform (as described in detail above with reference to FIG. 5). Source-driven resampling may be defined from the opposite perspective. As an example, ray-driven models may be destination-driven in the case of reprojection (thus verifying the condition of equation (6)) and may be source-driven in the case of backprojection. As another example, voxel-driven models may be destination-driven in the case of backprojection (thus verifying the condition of equation (8)) and may be source-driven in the case of reprojection.

In some examples, the one-dimensional homographic resampling transform described above may be known to be a homography in a flat-panel detector-based cone-beam tomographic geometry (e.g., wherein an X-ray detector is flat and all rays converge towards a focal point of an X-ray source, as described above with reference to FIG. 4) and may be implemented therefor. Such geometries are inherent to interventional X-ray C-arm systems, as well as all systems employed for performing cone-beam CT (CBCT) with a flat-panel X-ray detector. Specific applications of homographic generalization may include transforms that describe projections in parallel geometries (nuclear medicine) or digital breast tomosynthesis (DBT).

In other examples, such as in CT scanners having curved X-ray detectors, the function h(x) may not be a homography. One possible adaptation of homography-driven models to such systems includes performing a pre-sampling step of the CT imaging data, wherein a virtual X-ray detector for which the function h(x) is a homography may be constructed. Another possible adaptation of homography-driven models to such systems includes defining an ad hoc function modeling a geometry for which the function h(x) is a homography (at least locally). Advantageously, defining the ad hoc function in this way may be generalized to include imaging systems beyond flat-panel CT imaging systems.

Accordingly, in embodiments described herein, a more generalized and versatile expansion for homographic sampling is provided which may mitigate limitations of geometry-based models by providing discretization schemes based on a single set of basis functions which provide an adequate expansion for both reprojection and backprojection (e.g., an adequate resampling transform may be achieved in both source-driven and destination-driven uses of the expansion). In this way, the homography-based models described herein may enable recasting of the geometry-based models to achieve an analogous approach while avoiding the geometric representation altogether. Such recasting may increase ease of implementation on massively parallelized computational frameworks, e.g., GPU-based architectures.

Specifically, though some geometry-based models, such as distance-driven models, may be desirable for favorable image quality, highly sequential memory access patterns, and low arithmetic cost, facile massively parallel implementation may be difficult to achieve. For example, distance-driven algorithms may include an inner branching to adjust computation based on a relative position between voxel and detector cell (bin) edges (see FIG. 3). However, irregularity of resulting branching behavior may result in inefficiencies when implemented on massively parallel computing devices, e.g., GPUs.

Homography-based models may provide a more computationally efficient alternative by avoiding the inner branching, either by recasting the distance-driven model or by replacing the distance-driven model altogether. Further, homography-based models may outperform GPU implementations of geometry-based models both in terms of precision (e.g., via higher-order interpolation) and speed (e.g., via facile parallel implementation). Such precise and GPU-friendly computational schemes may be desirable for deep-learning based image reconstruction algorithms (e.g., via convolutional neural networks, which are often trained on GPU-based architectures).

It should be noted that geometrical considerations are not entirely absent from homography-driven interpolation. For example, the basis function $\beta_0(x)$ of the nearest-neighbor interpolation scheme may be uniform over a finite support. Since detection occurs at the finite detector surface, the basis function $\beta_0(x)$ may be well suited to describe a detector-level perspective of the tomographic geometry. From a voxel-level perspective, the basis function $\beta_0(x)$ may similarly assume a flat profile along a selected line of voxels. However, the geometrical interpretation in such cases is an order-0 discretization of the distribution—less than what may be assumed using the linear interpolation scheme (e.g., having an interpolation order of 1).

In some embodiments, homography-based models may further be coupled to footprint-based models (e.g., distance-driven models). Such coupling may be accomplished by bypassing the limitation of sampling being defined based on one sampling axis (e.g., the X-ray detector in ray-driven models, the sampling grid in voxel-driven models) while the other sampling axis is continuous and computed at a set of locations.

As indicated above, if a set of L functions (voxels) is defined along a sampling axis of the sampling grid, a given model is unchanged whatever the number K of bins of the X-ray detector. In the footprint-based models, the interaction between the voxels and bins may be explicitly quantified. In the homographic perspective, the sampling locations may be projected rather than a geometrical shape. For example, in the function u(x), the sampling along the axis u may be continuously changed with respect to x at a sampling rate of $s^2(x)$ (e.g., according to the magnification factor). Accordingly, when a grid sample is modeled at the location $x_l$, the fixed spacing $\delta_x$ may be assumed while ignoring the sampling rate being transformed by u(x) into a local sampling rate of spacing $\Delta_u$ as:

$$\Delta_u = u'(x)\delta_x = \frac{\delta_x}{s^2(x)} \quad (38)$$

To include the local sampling rate of spacing $\Delta_u$, a basis function $\xi_n(x)$ may be defined, where the basis function $\xi_n(x)$ may be a convolution of the basis function $\beta_{n,\delta_x}(x)$ for the fixed sampling $\delta_x$ with a basis function $\beta_{n,\Delta_u}(x)$ for the (transformed) local sampling rate of spacing $\Delta_u$. Without loss of generality, the fixed spacing $\delta_x$ may be set to 1 and a local sampling rate of spacing $\Delta_l$ may be defined as:

$$\Delta_l = u'(x_l)\delta_x \quad (39)$$

Each of L basis functions $\xi_{n,l}(x)$ (at the locations $x_l$) may then be defined as:

$$\xi_{n,l}(x) = \frac{1}{\Delta_l}\beta_{n,\Delta_l} * \beta_n(x) \quad (40)$$

The L basis functions $\xi_{n,l}(x)$ may expand p(u) and f(x) as:

$$p(u)=f(x)=\Sigma_l f_l \xi_{n,l}(x(u_k)-x_l) \quad (41)$$

and each of the K×L coefficients $r_{kl}$ may accordingly be obtained as:

$$r_{kl}=\xi_{n,l}(x(u_k)-x_l) \quad (42)$$

Alternatively, each of K basis functions $\chi_{n,k}(u)$ (at the locations $u_k$) may be defined as:

$$\chi_{n,k}(u) = \frac{1}{\Delta_k}\beta_{n,\Delta_k} * \beta_n(u) \quad (43)$$

where a local sampling rate of spacing $\Delta_k$ may be defined as:

$$\Delta_k=x'(u_k)\delta_u \quad (44)$$

and the (fixed) spacing $\delta_u$ is set to 1. The K basis functions $\chi_{n,k}(u)$ may expand f(x) and p(u) as:

$$f(x)=p(u)=\Sigma_k p_k \chi_{n,k}(u-u_k) \quad (45)$$

and each of the K×L coefficients $r_{kl}$ may accordingly be obtained as:

$$r_{kl}=\chi_{n,k}(u(x_l)-u_k) \quad (46)$$

Accordingly, and as above, two analogous models may be obtained (one in x and one in u) which each model fixed sampling and a homographic transformation thereof.

A special case where n=0 may be developed by considering the properties and definitions of equations (24)-(28). Assuming any sampling rate $\Delta>0$ and defining:

$$a_1 = \left|\frac{\Delta-1}{2}\right| \quad (47)$$

and $$a_2 = \frac{1+\Delta}{2} \quad (48)$$

then a convolution $\beta_{0,\Delta} * \beta_0(t)$ may be given as:

$$\beta_{0,\Delta} * \beta_0(t) = \begin{cases} \min(1,\Delta), |t| < a_1 \\ a_2 - |t|, a_1 \le |t| \le a_2 \\ 0, |t| > a_2 \end{cases} \quad (49)$$

Further, the convolution $\beta_{0,\Delta} * \beta_0(t)$ may be defined as:

$$\beta_{0,\Delta} * \beta_0(t) = \int_{-\infty}^{+\infty} \beta_0\left(\frac{t-\tau}{\Delta}\right)\beta_0(\tau)d\tau = \int_{-\frac{1}{2}}^{+\frac{1}{2}} \beta_0\left(\frac{x-\tau}{\Delta}\right)d\tau \quad (50)$$

such that the coefficients $r_{kl}$ may be computed as:

$$r_{kl} = \xi_{0,l}(x(u_k)-x_l) = \int_{x_l-\frac{1}{2}}^{x_l+\frac{1}{2}} \beta_0\left(\frac{x(u_k)-\tau}{\Delta_l}\right)d\tau \quad (51)$$

Considering equation (25), the integral of equation (51) is equal to an intersection of a support (originating at a bin) corresponding to function $\beta_0$ centered at the location $x_l$ and having a width of 1 with a footprint of the support (e.g., a projection of a bin) corresponding to function $\beta_{0,\Delta_l}$ centered at the location $x(u_k)$ and having a width of $\Delta_l$=u'($x_l$) (cf. equation (39)). The function $\beta_{0,\Delta_l}$ may therefore model a projection of a bin of an X-ray detector centered at the location $u_k$ and having a width $\delta_u$ as a projected bin centered at the location $x(u_k)$ and having a width $\Delta_l$=u'($x_l$).

The above description of the distance-driven model assumes an exclusively geometric representation, having cuboid voxels and uniform bins with order-0 basis functions on each side thereof. An interaction of the distance-driven model with the homography-driven model increases an interpolation order to 1 (e.g., the interpolation order of the linear interpolation scheme). To continue increasing precision, the footprint may be considered (rather than the support).

Specifically, an index m may be introduced to generalize the basis function $\xi_{n,l}(x)$ to a basis function $\xi_{n,m,l}(x)$, given as:

$$\xi_{n,m,l}=\beta_{m,\Delta_l} * \beta_n(x) \quad (52)$$

As such, each axis may be separately provided with an arbitrary high level of precision. In practice, an interpolation order of at least 1 may be desirable for each approach to the distribution sampling, such that any resulting model may have an interpolation order of at least 2.

Uniform bins and uniform voxels may further be assumed in the distance-driven model. The distance-driven model may further consider edges of the bins and the voxels along each (separable) direction. As described above with reference to FIG. 3, locations of the edges may further be projected onto an arbitrary common projection axis, forming sets of line segments (supports) of the bins and the voxels. Accordingly, the coefficient $r_{kl}$ may be set equal to the intersection over the projection axis between the support defined by a projection on the projection axis of a kth bin and a support defined by a projection on the projection axis of an lth voxel.

Coupling considerations of the footprint-based model to the homography-based model as described above may provide a model which may be equally suited for reprojection and backprojection, because the voxels, the detector, and the interaction therebetween may be simultaneously represented. Such a model may be correspondingly more computationally demanding.

To facilitate parallelization, the above-described interpolation scheme taking into account both the geometric and homographic representations may be rewritten assuming the projection axis is the axis u with the locations $u_k$ for the centers of the bins of the X-ray detector and locations $u(x_l)$ for the projections of the centers of the voxels onto the axis u. In this case, the function $u(x)$ may not be assumed to be a homography and therefore may not be approximated by magnifications. Instead, the function $u(x)$ may be used to determine the projection of the edges of an lth voxel having the width $\delta_x$. Projected supports of the voxels may form a set of L continuous line segments $S_l$, which may be given as $$S_l = \left[u\left(x_l - \frac{\delta_x}{2}\right), u\left(x_l + \frac{\delta_x}{2}\right)\right] \quad (53)$$

Similarly, projected supports of the bins may form a set of K continuous line segments $S_k$, which may be given as:

$$S_k = \left[u_k - \frac{\delta_u}{2}, u_k + \frac{\delta_u}{2}\right] \quad (54)$$

Accordingly, the (distance-driven) coefficient $r_{kl}$ may be given as:

$$r_{kl} = S_k \cap S_l \quad (55)$$

Determination of intersections may be based on determination of boundaries of the sets of segments $S_l$, $S_k$. However, excepting separability considerations, determining such boundaries may not be amenable to vectorization and parallelization.

The basis function $\beta_0$ may be used to develop an alternative approach, where the segment $S_k$ may be the support of a function $\beta_{0,1}(u-u_k)$ and the segment $S_l$ may be the support of a function $$\beta_{0,\frac{\delta_l}{\delta_u}}(u-u_l)$$

having a width $\delta_l$ given as:

$$\delta_l = u\left(x_l - \frac{\delta_x}{2}\right) - u_l \quad (56)$$

where the location $u_l$ may be defined as:

$$u_l = \frac{1}{2}\left(u\left(x_l - \frac{\delta_x}{2}\right) + u\left(x_l - \frac{\delta_x}{2}\right)\right) \quad (57)$$

As such, $r_{kl}$ may be given as:

$$r_{kl} = \int_{u_k-\frac{\delta_u}{2}}^{u_k+\frac{\delta_u}{2}} \beta_0\left(\frac{u_l - \tau}{\delta_l}\right)d\tau = \xi_{0,\delta_l}(u_l - u_k) \quad (58)$$

By employing the analytic definition of $\xi_{0,\delta_l}$ provided by equation (58), sorting operations may be avoided and algorithms may be developed with easily parallelizable function calls.

In the case of the flat-panel detector-based cone-beam tomographic geometry, and as discussed above, the resampling transform is a homography which may be locally approximated by a magnification factor given by $u'(x)$ or $x'(u)$. However, in one example, if the magnification factor is instead defined as a ratio of the segments $S_k$ and $S_l$, then the homography-driven interpolation described above may be an exact recast of the distance-driven model for the flat-panel detector-based cone-beam tomographic geometry.

Though expansions representing both a set of uniformly-spaced samples and a counterpart set of non-uniformly spaced samples are discussed above in the context of B-splines, in other examples, other families of basis functions (e.g., O-MOMS) may be used. In further examples, more complex expansions in more than one dimension may be devised (though with less separability).

Figure 6:
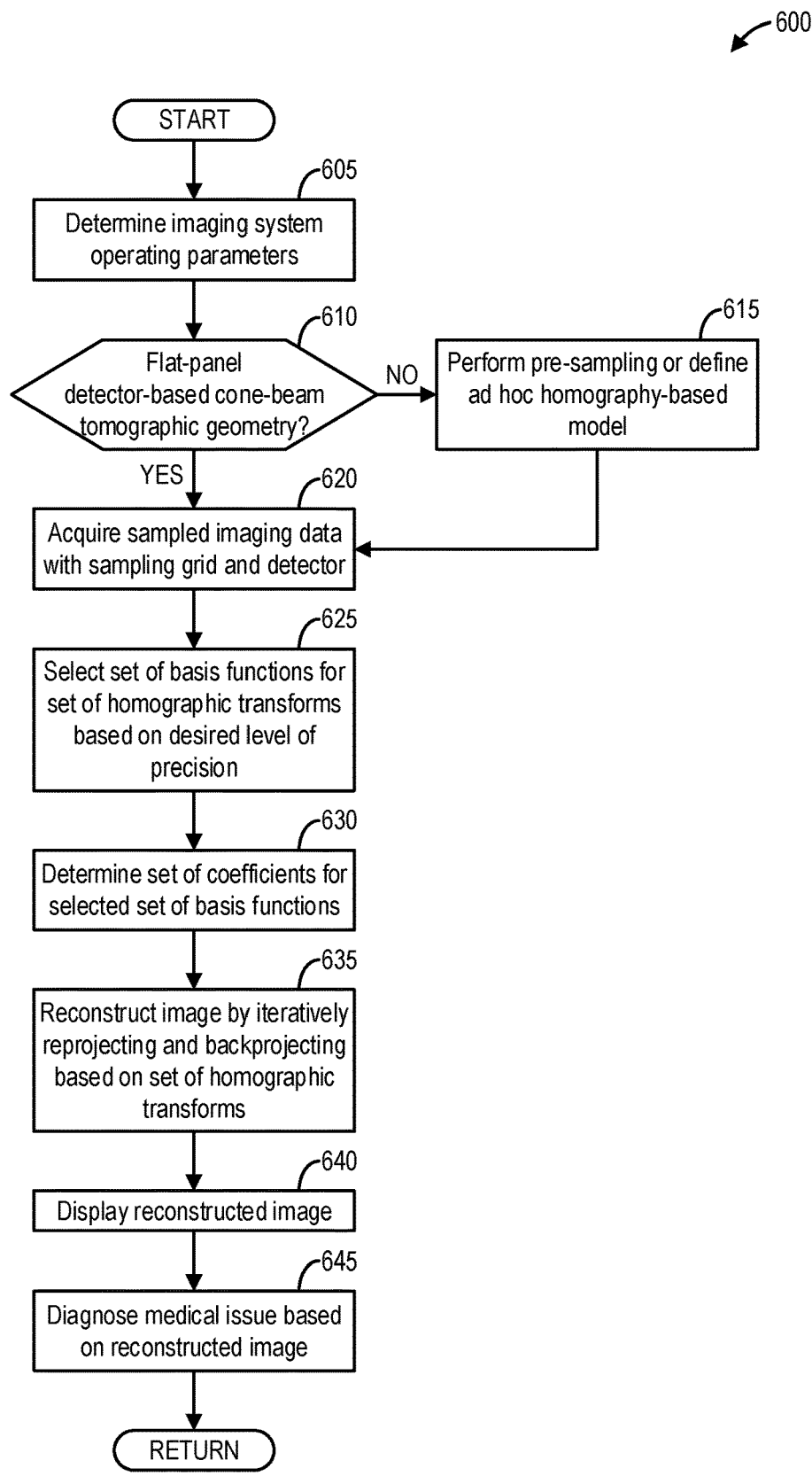
FIG. 6 shows a flow chart of a method for iterative image reconstruction via an exemplary homography-based model, according to an embodiment.

Referring now to FIG. 6, a flow chart showing a method 600 for iterative reconstruction via an exemplary homography-based model is depicted. As described below, a one-dimensional homographic resampling transform may be leveraged to resample sampled imaging data and form a symmetric projector/backprojector operator pair. Specifically, the symmetric projector/backprojector operator pair may be decomposed into a linear combination of transforms, each transform mapping a subset of the sampled imaging data to a single, continuous function, from which unknown sampling points may be determined via interpolation of known sampling points. As opposed to geometry-based models (e.g., models which are based on mapping the sampled imaging data to a set of geometric objects), the exemplary homography-based model recasts the resampled imaging data as one-dimensional basis functions which may expand and approximate the single, continuous function to an arbitrary level of precision. In some examples, a coefficient (e.g., weight) associated with each basis function may be determined substantially independently. In this way, a set of coefficients encoding the resampled imaging data may be determined in parallel, overcoming computational limitations of geometry-based models.

Method 600 is described below with regard to the systems and components depicted in FIGS. 1 and 2. For example, in some embodiments, method 600 may be implemented on the imaging system 200 of FIG. 2. However, it will be appreciated that method 600 may be implemented with other systems and components without departing from the scope of the present disclosure. In some embodiments, method 600 may be implemented as executable instructions in any of the medical imaging systems described above with reference to FIGS. 1 and 2. In one embodiment, method 600 may be implemented in non-transitory memory of a computing device, such as the computing device 216 of the imaging system 200 in FIG. 2. It will further be appreciated that individual steps discussed with reference to method 600 may be added, removed, substituted, or interchanged within the scope of the present disclosure.

At 605, method 600 may include determining one or more imaging system operating parameters. In one example, the one or more imaging system operating parameters may include an imaging protocol determining an initial configuration of an imaging source (e.g., an emitting device, an injected dye, etc.) and a detector for receiving imaging data. The imaging protocol may further determine movement of the imaging source and the detector relative to an object of interest, such that multiple images may be sequentially constructed.

In an additional or alternative example, the one or more imaging system operating parameters may include an imaging geometry. For example, the imaging geometry may include a relative positioning of the imaging source and the detector relative to the object of interest (e.g., as determined by the imaging protocol), as well as a specific imaging modality being leveraged. In some examples, the computing device may be coupled to a single imaging modality. In other examples, the computing device may be coupled to a plurality of imaging modalities (e.g., a plurality of imaging subsystems located at a same location or at different locations).

In an additional or alternative example, the one or more imaging system operating parameters may include a predefined homography-based model. Specifically, prior to acquiring imaging data via the imaging system, the one-dimensional homographic resampling transforms may be selected (e.g., based on the imaging protocol and/or the imaging geometry).

At 610, method 610 may include determining whether the imaging geometry is a flat-panel detector-based cone-beam tomographic geometry. For example, the computing device may determine the imaging geometry based on the one or more imaging system operating parameters. If the imaging geometry is not the flat-panel detector-based cone-beam tomographic geometry, method 600 may proceed to 615, where method 600 may include performing a pre-sampling routine or defining an ad hoc homography-based model. The one-dimensional homographic resampling transform described above may not be guaranteed to be a homography in all imaging systems. For example, the one-dimensional homographic resampling transform may not be a homography for a CT imaging system having a curved detector. Accordingly, a pre-sampling of the imaging data over a virtual detector for which a homography may be selected and implemented may be performed, or an ad hoc transform may be defined which at least locally models a desired imaging geometry.

If the imaging geometry is the flat-panel detector-based cone-beam tomographic geometry, or once the pre-sampling routine has been performed or the ad hoc homography-based model has been defined at 615, method 600 may proceed to 620, where method 600 may include acquiring sampled imaging data with a sampling grid and the detector. Specifically, the sampling grid may be partitioned into a plurality of voxels and the detector may be partitioned into a plurality of bins. A plurality of line integral measurements may be determined for each of the plurality of voxels and the plurality of bins from which an image may be reconstructed via an image reconstruction algorithm.

At 625, method 600 may include selecting the set of basis functions for the one-dimensional homographic resampling transforms based on a desired level of precision. Specifically, the one-dimensional homographic resampling transforms may resample the sampled imaging data by mapping the sampled imaging data to a single, continuous function to form the symmetric projector/backprojector operator pair. The set of basis functions may include a set of one-dimensional basis functions which may expand and approximate the single, continuous function to an arbitrary level of precision. In one example, a size of the set of basis function may be increased to correspondingly increase the level of precision. An interpolation scheme may further be selected to determine unknown points along the single, continuous function based on known points from the sampled imaging data. In this way, the symmetric projector/backprojector operator pair may provide a generalized framework in which the set of basis functions and the interpolation scheme may be selected to recast or match previously implemented algorithms or to provide novel handling of the sampled imaging data.

At 630, method 600 may include determining the set of coefficients (e.g., weights) for the selected set of basis functions. Specifically, each of the set of basis functions may be associated with a respective one of the set of coefficients. Each of the set of coefficients may encode an interaction between one of the plurality of distribution samples (e.g., sampled at points within respective voxels) and one of the plurality of bins in a matrix representation of either a projector or a backprojector of a given projector/backprojector operator pair. In some examples, each of the set of coefficients may be determined substantially independently, such that a massively parallelized algorithm (e.g., implemented on a GPU-based architecture) may be leveraged to compute each of the set of coefficients substantially simultaneously. Accordingly, computational limitations of geometry-based models may be ameliorated via the homography-based model described by embodiments herein.

At 635, method 600 may include reconstructing an image via iterative reprojection (e.g., forward projection) and backprojection (e.g., backward projection) based on the one-dimensional homographic resampling transforms. The symmetry of the symmetric projector/backprojector operator pair may be well-suited to such iterative image reconstruction, while also allowing arbitrary precision and computational efficiency via the selection of the set of basis functions, the interpolation scheme, and the independent determination of the set of coefficients. Accordingly, the homography-based model described by embodiments herein may be adaptable to deep-learning based image reconstruction techniques, which may leverage high-precision, massively-parallel algorithms to generate accurately reconstructed images.

At 640, method 600 may include displaying the reconstructed image. For example, the reconstructed image may be displayed to a user at a display device of a medical imaging system, such as the display device 232 of the imaging system 200 described in detail above with reference to FIG. 2.

At 645, method 600 may include diagnosing medical issue based on the (displayed) reconstructed image. For example, method 600 may include identifying a lesion depicted by the reconstructed image. In some examples, because the level of precision of the imaging data may be arbitrarily increased via selection of the basis set and the interpolation scheme, the lesion may be identified with greater accuracy relative to an image reconstruction algorithm having a fixed level of precision. Upon identification, the lesion may then be diagnosed as such, and as benign or malignant, after which treatment may be recommended. It will be appreciated that the diagnosis of the lesion is provided as an illustrative and non-limiting example, and that any one of a number of tissues, organs, or foreign objects within a subject may be identified based on the reconstructed image. It will further be appreciated that other embodiments disclosed herein may be directed to other applications beyond medical diagnostics, such as identification of one or more components of an inanimate object, for example.

In this way, an iterative image reconstruction method is provided which utilizes one-dimensional homographic resampling transforms. Specifically, a symmetric projector/backprojector pair made of a given set of one-dimensional homographic resampling transforms may be leveraged to satisfy mathematical constraints placed on iterative reprojection and backprojection paradigms while providing arbitrary levels of precision via basis set expansions of resampled functions. A technical effect of performing iterative reconstruction via such homography-based models is that geometric representations of lines of integration may be recast (e.g., generalized), or avoided altogether, resulting in a more easily and highly parallelizable algorithm. In some examples, embodiments of the iterative reconstruction model method may accordingly be implemented into massively parallel graphics processing unit architectures, which may concomitantly be adapted to deep learning techniques for image reconstruction.

In one embodiment, a method, comprising acquiring imaging data corresponding to a plurality of divergent X-rays, assigning a single functional form to the plurality of divergent X-rays, determining, via a homographic transform, weights of interaction between a plurality of distribution samples and a plurality of X-ray detector bins based on the single functional form, and reconstructing an image based on the weights of interaction. A first example of the method further comprises sampling the single functional form to obtain a desired level of precision. A second example of the method, optionally including the first example of the method, further includes wherein sampling the single functional form comprises expanding the single functional form with a set of one-dimensional basis functions. A third example of the method, optionally including one or more of the first and second examples of the method, further includes wherein each weight of the weights of interaction is associated with a respective one-dimensional basis function of the set of one-dimensional basis functions. A fourth example of the method, optionally including one or more of the first through third examples of the method, further includes wherein sampling the single functional form comprises determining unknown points corresponding to the single functional form by interpolating known points from the acquired imaging data. A fifth example of the method, optionally including one or more of the first through fourth examples of the method, further includes wherein the imaging data is sampled in a flat-panel detector-based cone-beam tomographic geometry. A sixth example of the method, optionally including one or more of the first through fifth examples of the method, further includes wherein the homographic transform is defined prior to acquiring the imaging data. A seventh example of the method, optionally including one or more of the first through sixth examples of the method, further includes wherein reconstructing the image comprises iteratively reconstructing the image with a symmetric projector/backprojector operator pair determined based on the weights of interaction. An eighth example of the method, optionally including one or more of the first through seventh examples of the method, further includes wherein the weights of interaction are determined in parallel. A ninth example of the method, optionally including one or more of the first through eighth examples of the method, further comprises diagnosing a medical issue based on the reconstructed image.

In another embodiment, a medical imaging system, comprising an X-ray source, an X-ray detector array configured to detect X-ray radiation emitted by the X-ray source and attenuated by an object of interest, and a controller communicably coupled to the X-ray detector array and storing instructions in non-transitory memory, the instructions executable to acquire sampled imaging data sampled over a sampling grid and bins of the X-ray detector array, select a set of basis functions for a set of homographic resampling transforms based on a desired level of precision, determine, in parallel, each coefficient of a set of coefficients for a respective one of the set of basis functions, reconstruct an image depicting the object of interest by iteratively reprojecting and backprojecting the sampled imaging data based on the set of coefficients, and display the reconstructed image. A first example of the system further includes wherein each basis function of the set of basis functions is globally continuous and independently computed. A second example of the system, optionally including the first example of the system, further includes wherein the instructions are further executable to select an interpolation scheme for the set of basis functions based on the desired level of precision. A third example of the system, optionally including one or more of the first and second examples of the system, further includes wherein the controller is further communicably coupled to a plurality of GPGPUs, the plurality of GPGPUs being configured to execute at least some of the instructions in parallel. A fourth example of the system, optionally including one or more of the first through third examples of the system, further includes wherein the image is reconstructed using a deep-learning based image reconstruction algorithm.

In yet another embodiment, a method for reconstructing an image from sampled imaging data, the method comprising resampling the sampled imaging data via a set of one-dimensional homographic resampling transforms to obtain resampled imaging data as a plurality of known sampling points, determining a plurality of unknown sampling points via interpolation of the plurality of known sampling points, forming a symmetric projector/backprojector operator pair based on the plurality of known sampling points and the plurality of unknown sampling points, and reconstructing the image by iteratively projecting and backprojecting the resampled imaging data via the symmetric projector/backprojector operator pair. A first example of the method further includes wherein determining the plurality of unknown sampling points via interpolation of the known sampling points comprises associating the plurality of known sampling points with the plurality of unknown sampling points to form a set of one-dimensional basis functions. A second example of the method, optionally including the first example of the method, further includes wherein forming the symmetric projector/backprojector operator pair comprises determining a set of coefficients respectively associated with the set of one-dimensional basis functions. A third example of the method, optionally including one or more of the first and second examples of the method, further includes wherein determination of the set of coefficients is performed analytically. A fourth example of the method, optionally including one or more of the first through third examples of the method, further includes wherein each one-dimensional basis function of the set of one-dimensional basis functions is formed as a convolution of B-spline functions.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring imaging data corresponding to a plurality of divergent X-rays;
   assigning a single functional form to the plurality of divergent X-rays;
   determining, via a homographic transform, weights of interaction between a plurality of distribution samples and a plurality of X-ray detector bins based on the single functional form;
   reconstructing an image based on the weights of interaction; and
   sampling the single functional form to obtain a desired level of precision, wherein a set of basis functions are selected for a set of homographic transforms based on the desired level of precision, and wherein a size of the set of basis functions is increased to correspondingly increase the level of precision.

2. The method of claim 1, wherein the set of basis functions is a set of one-dimensional basis functions, and wherein sampling the single functional form comprises expanding the single functional form with the set of one-dimensional basis functions.

3. The method of claim 2, wherein each weight of the weights of interaction is associated with a respective one-dimensional basis function of the set of one-dimensional basis functions.

4. The method of claim 1, wherein sampling the single functional form comprises determining unknown points corresponding to the single functional form by interpolating known points from the acquired imaging data.

5. The method of claim 1, wherein the imaging data is sampled in a flat-panel detector-based cone-beam tomographic geometry.

6. The method of claim 1, wherein the homographic transform is defined prior to acquiring the imaging data.

7. The method of claim 1, wherein reconstructing the image comprises iteratively reconstructing the image with a symmetric projector/backprojector operator pair determined based on the weights of interaction.

8. The method of claim 1, wherein the weights of interaction are determined in parallel.

9. The method of claim 1, further comprising diagnosing a medical issue based on the reconstructed image.

10. A medical imaging system, comprising:
    an X-ray source;
    an X-ray detector array configured to detect X-ray radiation emitted by the X-ray source and attenuated by an object of interest; and
    a controller communicably coupled to the X-ray detector array and storing instructions in non-transitory memory, the instructions executable to:
    acquire sampled imaging data sampled over a sampling grid and bins of the X-ray detector array;
    select a set of basis functions for a set of homographic resampling transforms based on a desired level of precision;
    determine, in parallel, each coefficient of a set of coefficients for a respective one of the set of basis functions;
    reconstruct an image depicting the object of interest by iteratively reprojecting and backprojecting the sampled imaging data based on the set of coefficients; and
    display the reconstructed image,
    wherein the controller is further communicably coupled to a plurality of GPGPUs, the plurality of GPGPUs being configured to execute at least some of the instructions in parallel.

11. The system of claim 10, wherein each basis function of the set of basis functions is globally continuous and independently computed.

12. The system of claim 10, wherein the instructions are further executable to select an interpolation scheme for the set of basis functions based on the desired level of precision.

13. The system of claim 10, wherein the image is reconstructed using a deep-learning based image reconstruction algorithm.

14. A method for reconstructing an image from sampled imaging data, the method comprising:
    resampling the sampled imaging data via a set of one-dimensional homographic resampling transforms to obtain resampled imaging data as a plurality of known sampling points;
    determining a plurality of unknown sampling points via interpolation of the plurality of known sampling points;
    forming a symmetric projector/backprojector operator pair based on the plurality of known sampling points and the plurality of unknown sampling points; and
    reconstructing the image by iteratively projecting and backprojecting the resampled imaging data via the symmetric projector/backprojector operator pair,
    wherein the image is reconstructed using a deep-learning based image reconstruction algorithm.

15. The method of claim 14, wherein determining the plurality of unknown sampling points via interpolation of the known sampling points comprises associating the plurality of known sampling points with the plurality of unknown sampling points to form a set of one-dimensional basis functions.

16. The method of claim 15, wherein forming the symmetric projector/backprojector operator pair comprises determining a set of coefficients respectively associated with the set of one-dimensional basis functions.

17. The method of claim 16, wherein determination of the set of coefficients is performed analytically.

18. The method of claim 15, wherein each one-dimensional basis function of the set of one-dimensional basis functions is formed as a convolution of B-spline functions.

* * * * *